United States Patent [19]

Matsumura

[11] 4,265,518
[45] May 5, 1981

[54] VARIABLE MAGNIFICATION APPARATUS HAVING ILLUMINATION COMPENSATING ABILITY

[75] Inventor: Isao Matsumura, Yokosuka, Japan

[73] Assignee: Canon Kabushiki Kaisha, Tokyo, Japan

[21] Appl. No.: 919,149

[22] Filed: Jun. 26, 1978

[30] Foreign Application Priority Data

Jun. 30, 1977 [JP] Japan .................................. 52-78401
May 12, 1978 [JP] Japan .................................. 53-56257

[51] Int. Cl.³ .............................................. A61B 3/14
[52] U.S. Cl. ........................................ 351/7; 351/8; 351/9; 351/13; 351/16
[58] Field of Search ............... 351/7, 8, 9, 13, 16; 354/62, 126, 196; 350/184, 186

[56] References Cited

U.S. PATENT DOCUMENTS 3,549,250 12/1970 Pantenburg ............... 350/184 X
3,915,564 10/1975 Urban ............................. 351/7

FOREIGN PATENT DOCUMENTS

Z 4717 4/1956 Fed. Rep. of Germany ........... 350/184
1129603 9/1956 France ........................................ 351/7

*Primary Examiner*—Paul A. Sacher
*Attorney, Agent, or Firm*—Fitzpatrick, Cella, Harper & Scinto

[57] ABSTRACT

Apparatus herein disclosed comprises a photographing system having an optical system of variable magnification and an illumination system having a light source for photographing and a light source for observing. In the apparatus, the existing photographing magnification of the optical system is detected and the quantity of light incident upon a film or a finder visual field is controlled depending upon the detected magnification so as to obtain an optimum exposure to the film of the photographing system or to maintain the brightness of the visual field constant. To attain the control of quantity of light, light passing through the illumination system or light passing through the optical system is gradually reduced with widening of the angle of field. Alternatively, intensity of light emitted from the light source for observing or light emitting time of the light source for photographing is altered depending upon the detected magnification.

34 Claims, 23 Drawing Figures

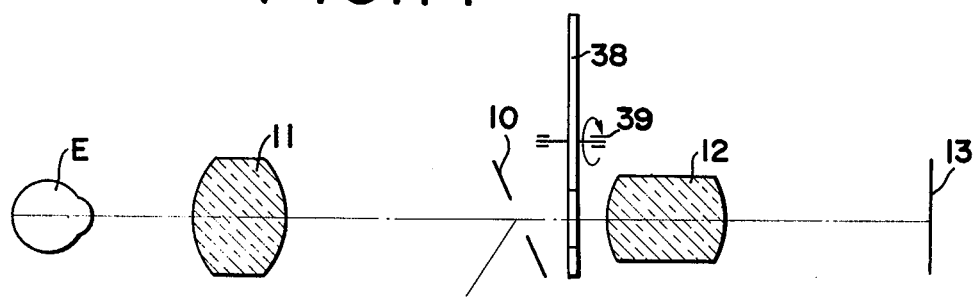
FIG.14
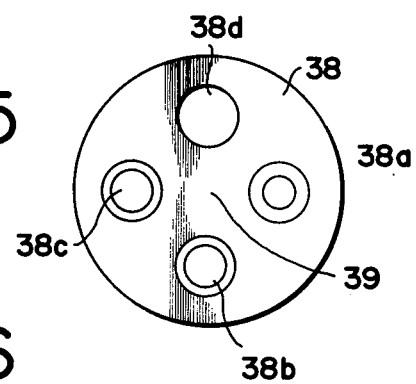
FIG.15
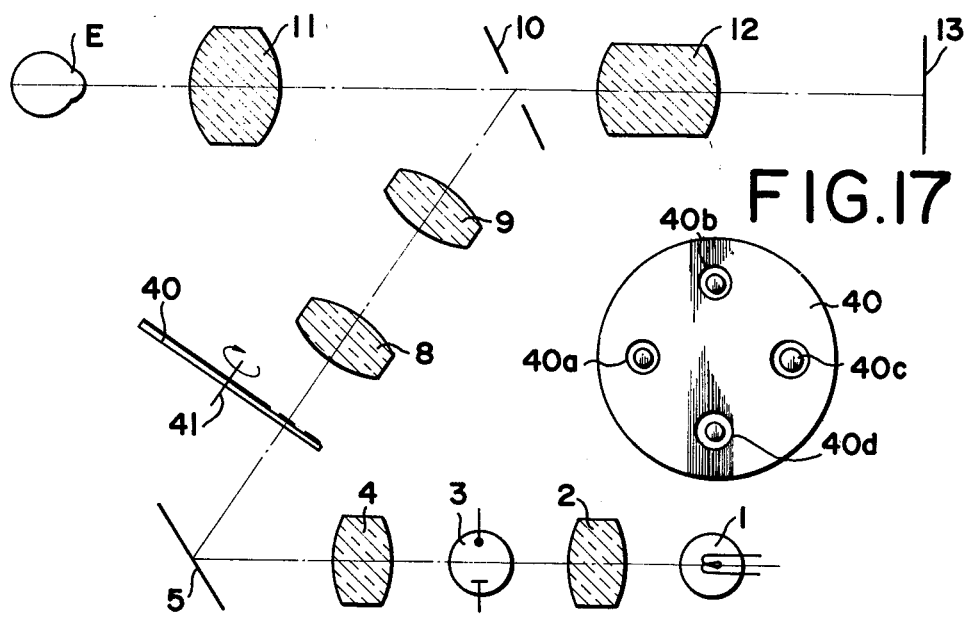
FIG.16
FIG.17

VARIABLE MAGNIFICATION APPARATUS HAVING ILLUMINATION COMPENSATING ABILITY

BACKGROUND OF THE INVENTION

1. Field of the Invention

The present invention relates to apparatus used for observing an object such as the eye fundus or for taking a picture of it while illuminating the object with artificial light, and also relates to apparatus in which magnification for observing or photographing is variable.

2. Description of the Prior Art

Recently, a great emphasis has been placed on the prevention against diseases of adults and examination of the eye has been increasingly conducted for this purpose. A photo-picture of the fundus of the eye gives useful information for diagnosis of diseases of adults. For this reason, there is an increasing tendency to carry out photographing of fundus of the eye in a group. As a reflection of this tendency, it has been desired to provide a such fundus camera of wide picture angle with which a broader area of the fundus can be photographed a smaller number of times. On the other hand, it is also desired to provide a fundus camera which allows photography of the fundus with a narrow picture angle and in a higher magnifying power for the purpose of close examination of those eyes in which some morbid changes have been found at the time of a group examination.

However, it is very difficult to successfully take an enlarged picture of an object while maintaining the size of film or the area of finder visual field unchanged. Due to shortage of quantity of light, the film is insufficiently exposed to light. Also, the visual field becomes too dark to observe the object.

SUMMARY OF THE INVENTION

Accordingly, it is an object of the invention to provide the above mentioned type of apparatus which permits an optimum exposure of the photosensitive medium even when the magnification of the optical system is changed.

It is another object of the invention to provide the above mentioned type of apparatus which permits maintenance of the brightness of the visual field even when the magnification is changed.

It is a further object of the invention to provide means for controlling the quantity of light or the time of illumination by a source for photographing by a fundus camera in accordance with the photographing magnification of the photographing optical system.

It is a still further object of the invention to provide means for reducing the quantity of light illuminating an object or light reflected by the object in proportion to the decrease of magnification of an ophthalmic observation apparatus.

An even further object of the invention is to provide means for controlling the intensity of light from the light source for observation in an ophthalmic observation apparatus in accordance with the observing magnification.

Other and further objects, features and advantages of the invention will appear more fully from the following description.

BRIEF DESCRIPTION OF DRAWINGS

FIG. 8 illustrates the use of an attachment lens for enlargement wherein

FIG. 14 schematically shows a fifth embodiment of the invention;

FIG. 15 is a plan view of a multi-stop plate;

FIG. 16 shows a sixth embodiment of the invention;

FIG. 17 is a plan view of a multi-ring slit plate;

DESCRIPTION OF THE PREFERRED EMBODIMENTS

Figure 1:
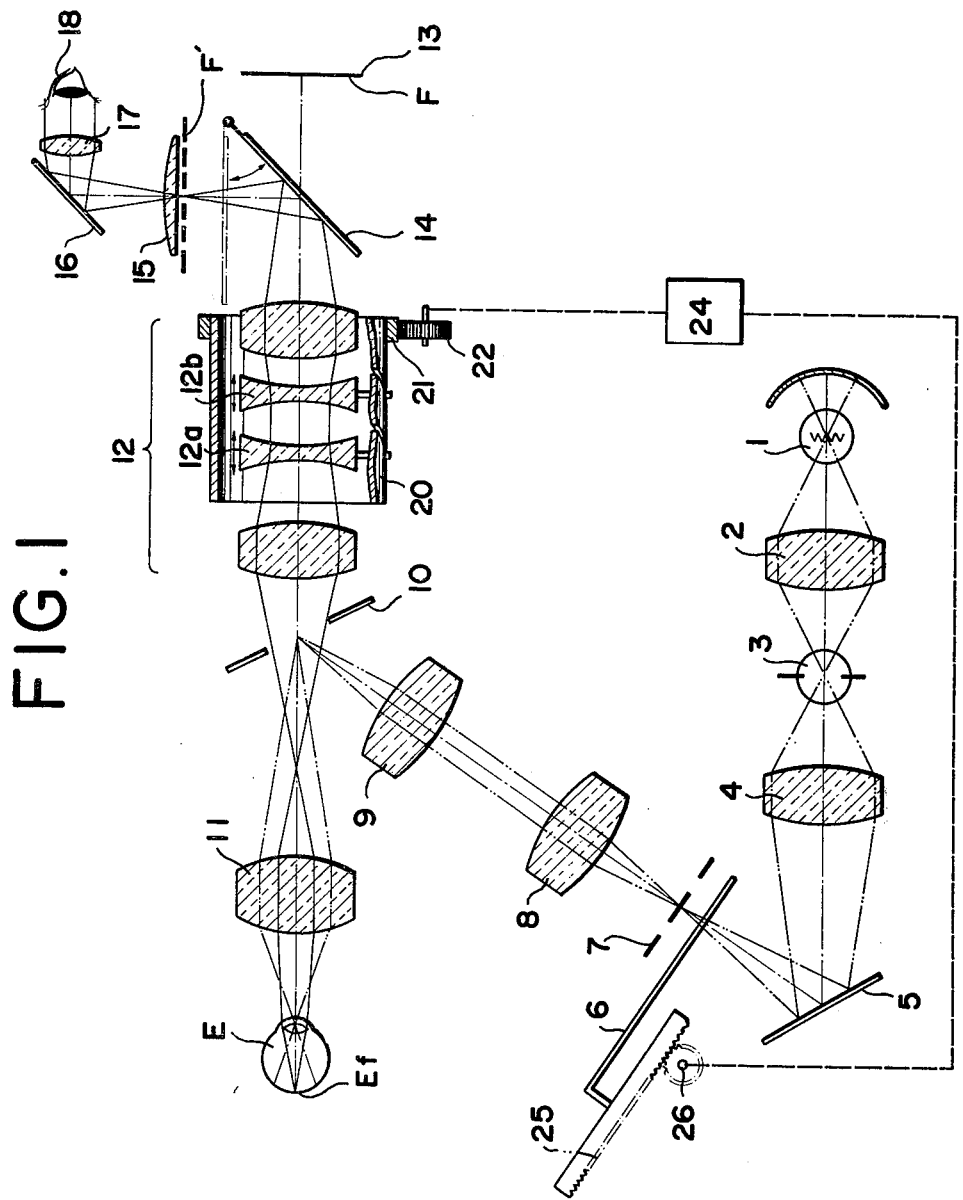
FIG. 1 schematically shows a first embodiment of the invention.

Referring first to FIG. 1, there is shown an embodiment of the present invention.

Figure 2:
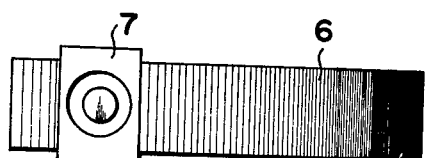
FIG. 2 is a plan view of a filter the intensity of which continuously changes and a slit plate used in the embodiment.

In FIG. 1, the reference character E designates a human eye to be examined and Ef is the fundus of the eye. 1 is a lamp for observing, 2 is a first condenser lens, 3 is a strobo tube, such as a Xenon tube for photographing, 4 is a second condenser lens, 5 is a light path deflecting mirror, 6 is a filter the intensity of which gradually changes, and 7 is a slit plate having a ring aperture therein. The filter 6 and slit plate 7 are shown in detail in FIG. 2 in a plan view. As the filter 6 moves, the quantity of light passing through the ring aperture of the slit plate changes. The beam of light emitted from the lamp 1 as well as the of light emitted from the strobe tube 3 converges on the slit plate 7.

8 and 9 are relay lenses, 10 is a bored mirror having a diaphragm aperture therein and 11 is an objective lens. Bored mirror 10 and slit plate 7 are conjugate relative to relay lenses 8 and 9. Also, bored mirror 10 and the pupil of testing eye positioned in a predetermined position are conjugate relative to the objective lens 11.

12 is an imaging lens, 13 is a film and F is image plane of the imaging lens. An image of the fundus Ef is once imaged by the objective lens 11 and then it is again re-imaged on the film 13 by the imaging lens 12.

14 is a jump-up mirror, 15 is a field lens, 16 is a light path deflecting mirror, 17 is an eyepiece and 18 is an examiner. Designated by F' is image plane (image plane for observing) of the imaging lens through the jump-up mirror 14.

The above mentioned imaging lens 12 is a variable focus lens. Designated by 12a and 12b a so-called variator and compensator, respectively, which are able to shift in the direction of the optical axis. 20 is a cam tube on which cam slots are formed. Engaged in the cam slots are pins connected with the lenses 12a and 12b respectively. In the direction of the optical axis a each pin is also in engagement with a straight cam tube although not shown in the drawing. Around the cam tube 20 there is formed a gear part in mesh with a pinion 22. The pinion 22 is driven by a driving part 24. Connected with the filter having a gradient of intensity 6, is a rack 25 which is in mesh with a pinion 26 driven by the driving part 24.

The cam tube 20 is rotated by operating the driving part 24. This rotational movement of the cam tube causes the lenses 12a and 12b to shift so that the focal length of the imaging lens 12 is changed. At the same time, the intensity changing filter 6 is also shifted in proportion to the change in focal length of the imaging lens 12. As a result, the quantity of light incident upon the film plane 13 or upon the image plane F' is maintained constant. Before reaching the film plane 13 or the image plane F', the beam of illuminating light passed through the ring opening of the plate 7, is reflected upon the fundus Ef and then passes through the objective lens 11 and the imaging lens 12. With the increase in magnification of the imaging lens 12, the quantity of light transmitted through the slit plate 7 is gradually increased because of higher transmissivity of the portion of the filter 6 then overlapped on the slit plate 7.

The manner of operation of the above described apparatus is as follows:

When the lamp 1 is put on, the beam of light emitted from it enters the condenser lens 2 by which the beam is converged. After converging, the beam diverges and enters the condenser lens 4 by which the beam is again converged, and the mirror 5 deflects it to the graduated intensity filter 6. The quantity of light transmitted through the filter 6 is adjusted by the transmissivity of the filter depending upon the focal length of the imaging lens 12. The beam then passes through the ring slit of the slit plate 7 and it is once imaged on the bored mirror 10 by the action of relay lenses 8 and 9. Thereafter the beam illuminates the fundus Ef through the objective lens 11. Object light reflected by the fundus Ef is reflected by the jump-up mirror 14 after passing through the objective lens 11 and the imaging lens 12. The reflected object light forms an image of the fundus on the observing image plane F' which image is observed by the examiner through field lens 15, mirror 16 and eyepiece 17.

Figure 3:
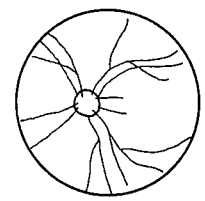
FIG. 3 illustrates a visual field of a finder in low magnification.
Figure 4:
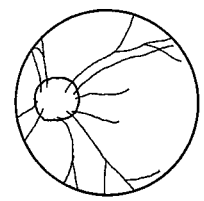
FIG. 4 illustrates a visual field of a finder in high magnification.

Assuming that viewing the observation visual field shown in FIG. 3, the examiner wished to view the observing portion of the fundus in more enlarged view, then the examiner operates the driving part 24 to rotate the cam tube 20. As the cam tube 20 rotates, lenses 12a and 12b move along the cam slots so that the focal length of the imaging lens 12 is increased. At the same time, the filter of changing intensity 6 is shifted in the direction to increase the quantity of light transmitted through the filter. Therefore, the examiner can view a magnified observing view field as illustrated in FIG. 4 without any change in brightness of the view field.

To take a picture of the fundus, the examiner makes the mirror 14 jump up and then makes the strobo tube 3 flash. Since the quantity of strobo light entering the film plane is also adjusted in the same manner, it is assured to expose the film 13 to a proper exposure light.

Figure 5:
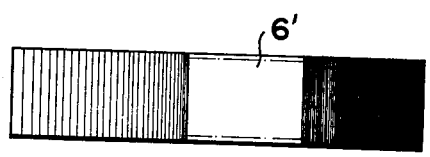
FIG. 5 is a plan view of a filter the intensity of which changes stepwise.

FIG. 5 shows another example of a filter, the intensity of which changes. In this example, the filter is divided into several sections having different intensities each other. The intensity of the filter changes regularly step by step. The shift of this filter is carried out intermittently. In accordance with this stepwise change of intensity in the filter, the imaging lens 12 is so designed that its focal length is changed also stepwise.

Now, referring to FIGS. 6 through 10, other embodiments of the invention are described particularly concerning means for changing the magnification of the optical system interposed between the testing eye and the image plane for photographing or for observing. In these figures, the same reference numerals and characters as used in FIG. 1 indicate the same members and elements as those shown in FIG. 1.

Figure 6:
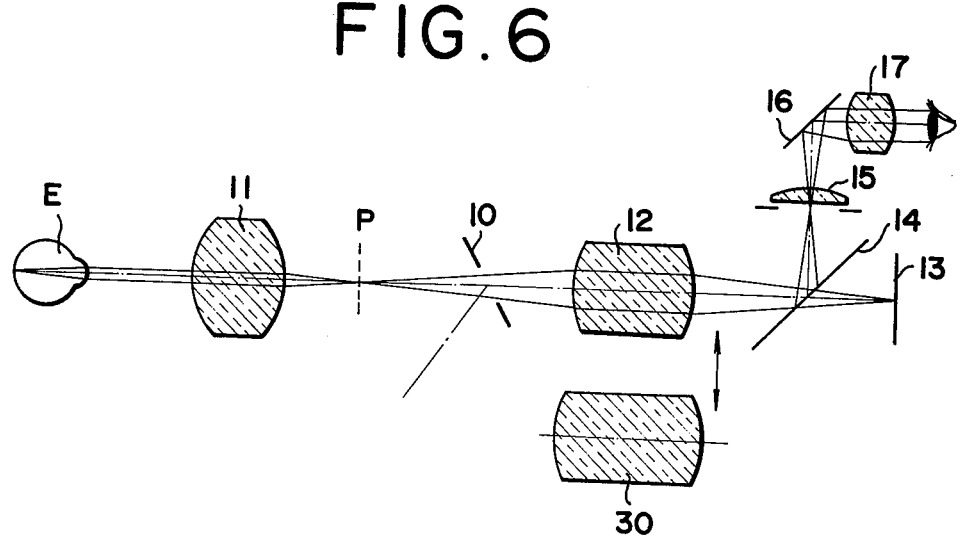
FIG. 6 schematically shows the essential part of a second embodiment of the invention.

In the embodiment of FIG. 6, the whole imaging lens 12 is so arranged as to be exchangeable for a converging lens having a different focal length 30. When mounted, the object plane of the exchangeable lens 30 is to be coincident with the image plane P of the objective lens 11 whereas the image plane of the lens is coincident with the film plane 13.

Figure 7:
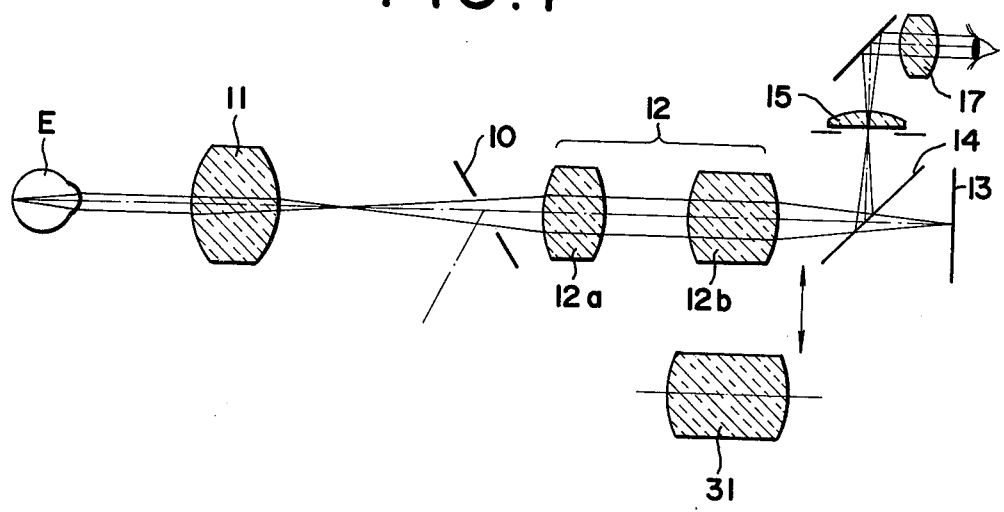
FIG. 7 is a similar view to FIG. 6 showing a third embodiment of the invention.

In case of the FIG. 7 embodiment, a part of the imaging lens 12 is exchanged for other lens having a different focal length. To this end, the imaging lens 12 is composed of a fixed fore-lens group 12a and a removable rear-lens group 12b. The rear-lens group 12b is exchanged for a lens group 31 having a different focal length to change the resultant magnification.

Figure 8A:
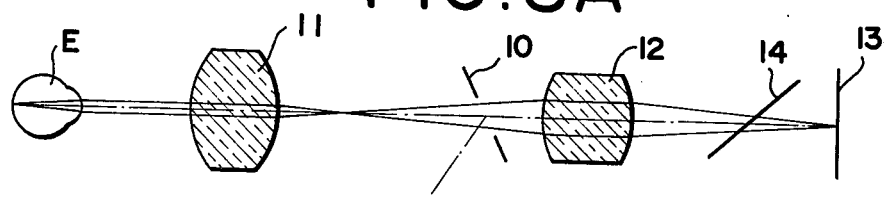
FIG. 8A is a view before mounting and FIG. 8B is a view after mounting the attachment lens.
Figure 8B:
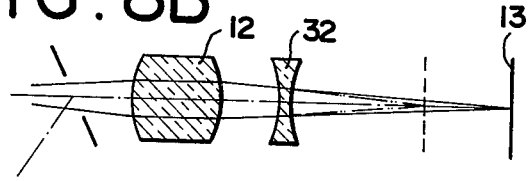

In the embodiment of FIG. 8, an attachment lens is placed in the light path for photographing to change the resultant focal length. More particularly, in the optical system shown in FIG. 8a, a diverging lens 32 is additionally interposed as illustrated in FIG. 8b. The insertion of the lens 32 results in an increase of the focal length of the optical system. But, the position of the image plane is shifted rearward at the same time.

For such type of fundus camera as shown in FIG. 1, the focus adjusting method most commonly used is to shift the whole body or a part of the imaging lens in the direction of optical axis or to alter the distance between the imaging lens and the jump-up mirror.

If the embodiment of FIG. 8 where an attachment lens 32 is used for changing the magnification is applied to such type of fundus camera in which the distance between the imaging lens and the jump-up mirror is changed, the shift of the image plane may be compensated for by shifting the film plane 13 in a simple manner.

Figure 9A:
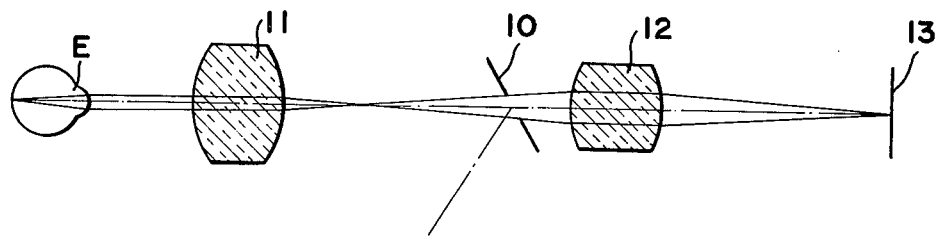
FIG. 9 is a similar view to FIG. 8 illustrating the use of another attachment lens for enlargement.
Figure 9B:
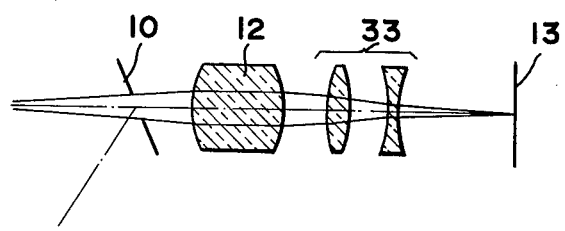

According to the embodiment shown in FIG. 9, there is used a magnification variation lens 33 composed of at least two lens groups to change the magnification of an optical system as shown FIG. 9a. The variation lens 33 is interposed in the optical system behind the imaging lens.

Figure 10:
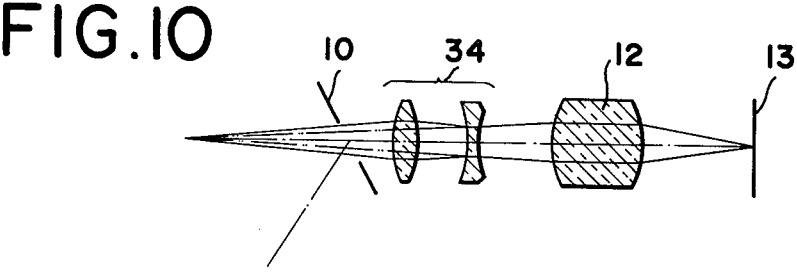
FIG. 10 illustrates another example of an attachment lens for enlargement.

In case of the embodiment of FIG. 10, a variation lens 34 is interposed immediately before the imaging lens.

While in the above described embodiments, the magnification of the optical system is variable only by two steps, possibility of changing magnification by three or more steps may be given by preparing a number of attachment lenses having different focal lengths or variation lenses for this purpose. Also, the objective lens 11 may be exchanged for other objective lenses to attain the same object.

In order to maintain constant the quantity of light incident upon the image plane, there may be used various light control methods other than the above described method shown in the first embodiment of FIG. 1. Examples of other light control methods are shown in FIGS. 11 through 19 respectively.

Figure 11:
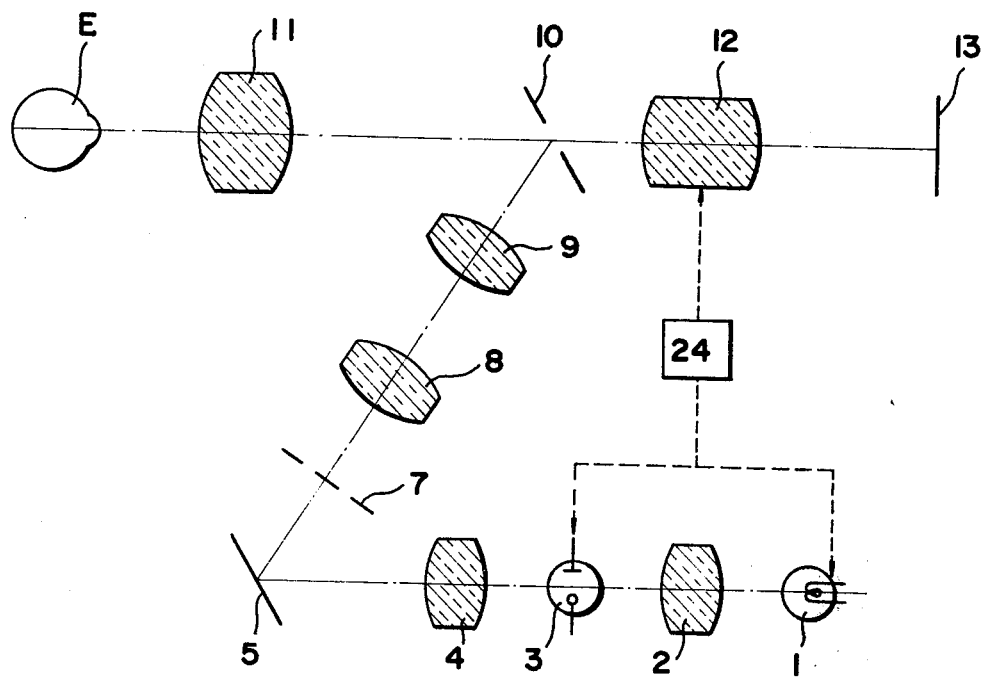
FIG. 11 schematically shows a fourth embodiment of the invention.
Figure 12:
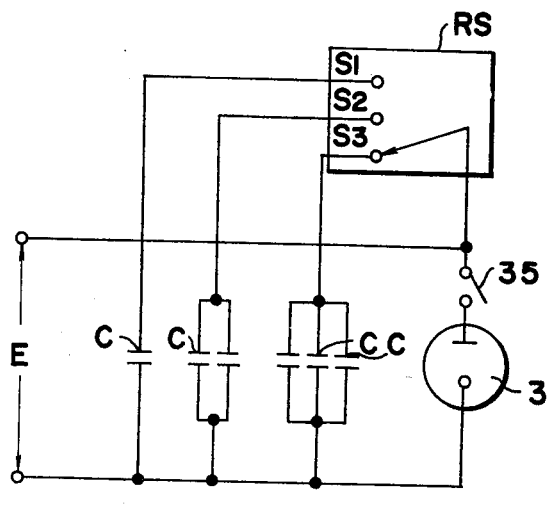
FIG. 12 is a block diagram of an electric circuit for controlling the light source for photographing.
Figure 13:
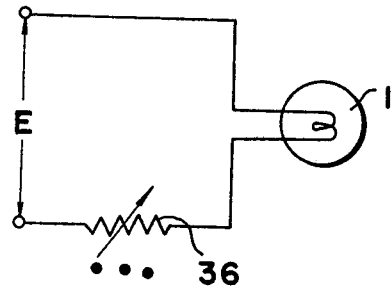
FIG. 13 is a block diagram of an electric circuit for controlling the light source for observing.

In the embodiment shown in FIGS. 11, 12 and 13, the quantity of light emitted from the light source is controlled in order to keep the quantity of light entering the image plane always constant.

With the arrangement of FIG. 11, the quantity of light from the strobo 3 or the light source for observation 1 is changed by operating the driving part 24 while changing the focal length of imaging lens 12 employing a zooming method (FIG. 1), lens exchanging method (FIGS. 6 and 7) or variation lens attaching method (FIGS. 8, 9, 10).

As seen in FIG. 12, the quantity of strobo light is controlled by changing over the capacity of the condenser. To this end, there are arranged in parallel condensers grouped in several sets (three sets are shown in FIG. 12), the number of condensers C contained in each set being different from each other. By operating a change-over switch, one of the contacts $S_1$, $S_2$ and $S_3$ is selected to selectively charge any one of the sets of condensers. Thus, when a trigger switch 35 is turned on, the strobo tube 3 emits light in a quantity then selected.

On the other hand, as seen in FIG. 13, the quantity of light from the lamp for observation 1 is controlled by changing-over the resistance of a variable resistor 36. The resistor 36 and the lamp 1 are connected to the power source in series. In the shown embodiment, the value of resistance is variable between three steps to change the quantity of light.

In this manner, when the magnification of the imaging lens 12 shown in FIG. 11 is changed, the rotary switch RS shown in FIG. 12 is changed over to select any one of the contacts $S_1$, $S_2$ and $S_3$. Also, at the same time, the resistance value of the variable resistor 36 is changed. Therefore, for observing or for photographing the object, the quantity of light falling upon the image plane or the observing image plane is maintained unchanged irrespective of the changed magnification of the optical system.

FIG. 14 shows another arrangement used for controlling the quantity of light incident upon the image plane. In this embodiment, the control of light is effected by controlling the opening of a diaphragm aperture for the optical system. In FIG. 14, the reference numeral 38 designates a multi-diaphragm plate (which is also mentioned as a multi-stop plate) and 39 is a rotation axis of the plate. The structure of the multi-stop plate 38 is seen in detail in FIG. 15. In the plate 38, there are provided diaphragm apertures 38a, 38b, 38c and 38d with their cross-sectional areas being different from each other. By rotating the plate 38, a desired diameter of diaphragm aperture can be selected. According to the embodiment, the quantity of light on the image plane is controlled by the rotation of the multi-stop plate 38 interlocked with the movement of the imaging lens 12 for changing the magnification, without necessity of changing the quantity of emitted light from the strobo tube or the lamp for observing.

According to another embodiment shown in FIG. 16, the quantity of light incident upon the eye fundus is controlled by altering the cross-sectional area of ring slit aperture of a slit plate interlocking with the change in magnification of the optical system. Designated by 40 is a rotary plate having a rotation axis 41. As seen in detail in FIG. 17, the rotary plate 40 is provided with ring slit apertures 40a, 40b, 40c and 40d formed therein with their areas being different from each other (the size of the center spot is the same for every aperture). In linkage with the magnification changing motion of the imaging lens 12, a certain one of slit apertures is selectively interposed in the optical path. Thus, if the photographing magnification of the imaging lens 12 is increased, then the quantity of light illuminating the fundus is increased accordingly.

Figure 18:
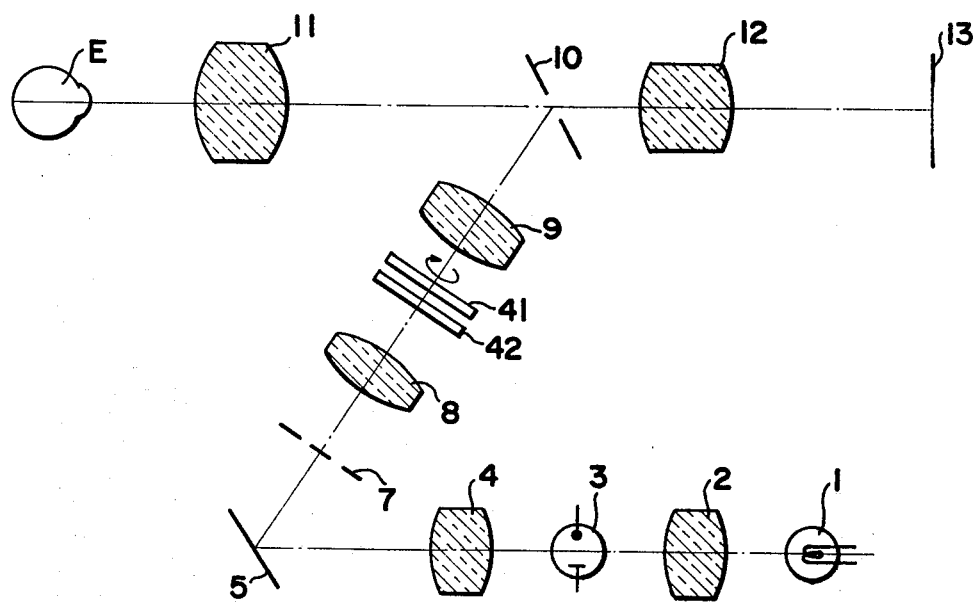
FIGS. 18, 19 and 20 show different embodiments of the invention respectively.

FIG. 18 shows a further example of a light control system wherein a polarization plate is used to control the quantity of illuminating light. Interposed between the two relay lenses 8 and 9 is light control means which comprises an analizer 41 and a polarizer 42. By rotating any one of two elements 41 and 42 around the optical axis, the quantity of light passed therethrough is changed. Therefore, the quantity of light on the image plane can be maintained constant by changing the relative rotational angle between the two elements 41 and 42 in accordance with the change in magnification of the imaging lens 12.

Figure 19:
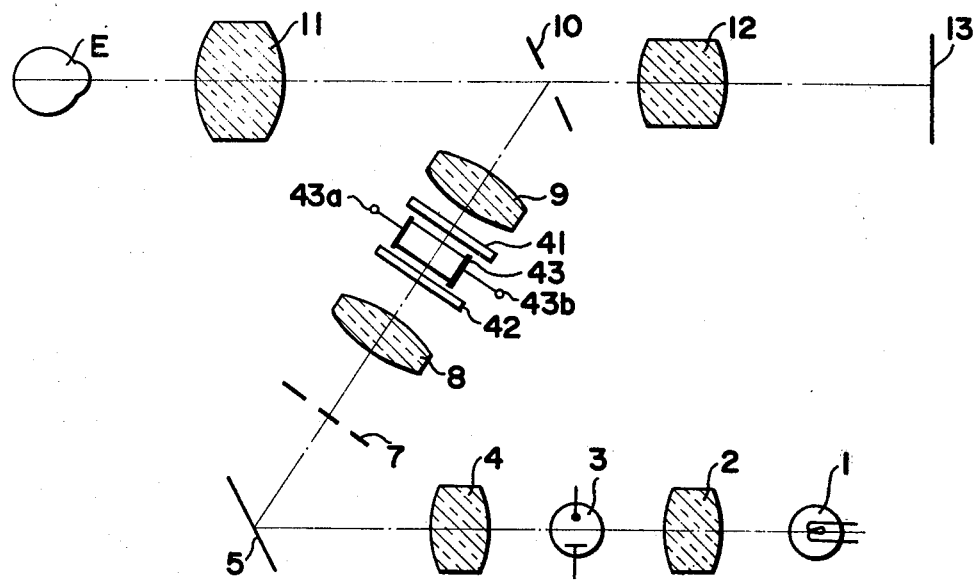

According to a still further embodiment shown in FIG. 19, Kerr cell effect is used to control the quantity of illuminating light. Again, the reference numerals 41 and 42 designate an analizer and a polarizer respectively which are fixed in this case. 43 is a Kerr cell and 43a and 43b are terminals to which voltage is applied. By changing the voltage applied to the terminal 43a and 43b, the light transmissivity of light modulating means comprising the analyses, Kerr cell and polarizer, is changed. Therefore, the quantity of light reaching the image plane for photographing or the image plane for observing is kept constant by changing the voltage applied to the Kerr cell in linkage with the magnification changing motion of the imaging lens 12.

Figure 20:
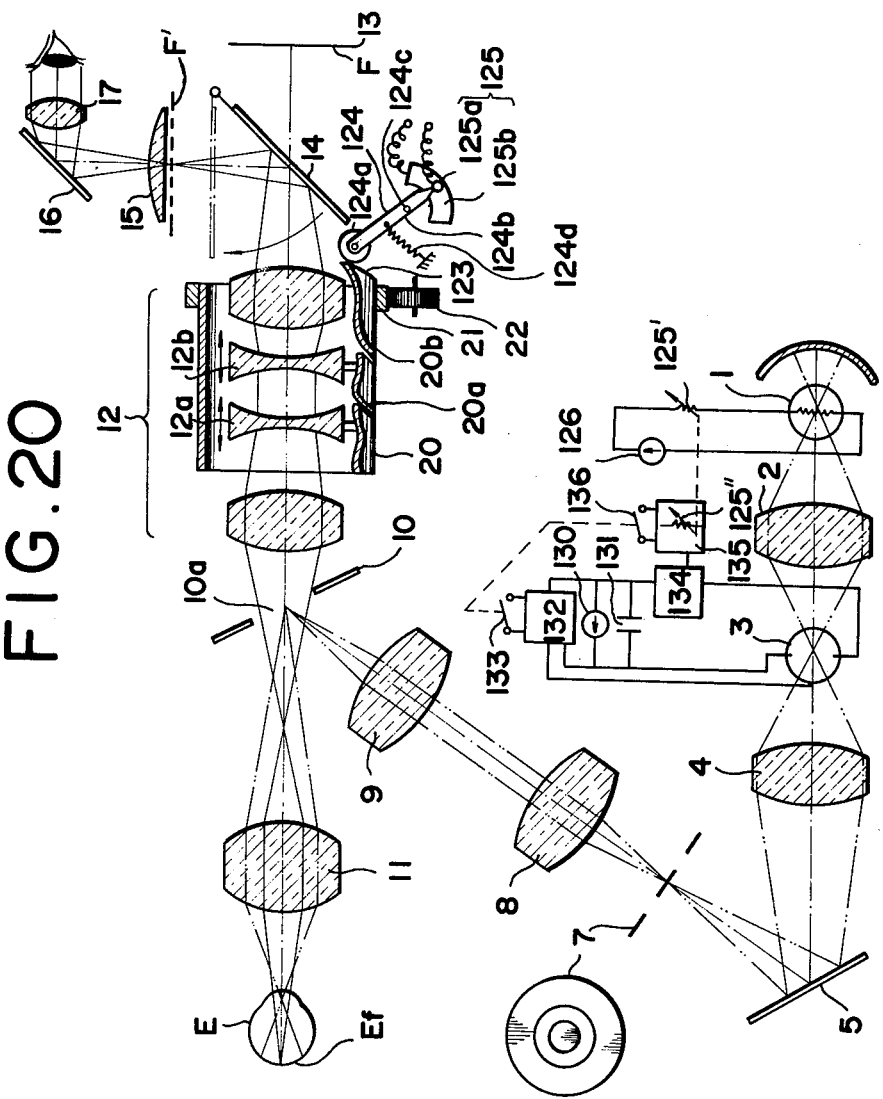

Referring now to FIG. 20, another embodiment of the invention will be described in detail.

In FIG. 20 the reference character E designates again a human eye to be examined and Ef is the fundus of the eye. 1 is an incandescent lamp for observation and 2 is a first condenser. 3 is a xenon tube, 4 is a second condenser, 5 is a light path deflecting mirror and 7 is a slit plate having a center screen portion for incident light and a slit aperture around the center screen portion. The incandescent lamp 1 and the xenon tube 3 are conjugated with respect to the first condenser lens 2. The xenon tube 3 and the slit plate 7 are conjugated with respect to the lens 4.

Designated by 8 and 9 are relay lenses and 10 is a tilted mirror having a central aperture formed therein. 11 is an objective lens opposed to the testing eye. The slit plate 7 and the tilted mirror 10 are approximately conjugate, and also the slit plate 7 and the cornea or pupil of the testing eye are conjugate with respect to the relay lens group 8, 9, the tilted mirror 10 and the objective lens 11. The above-mentioned elements 1–11 constitute an illuminating system.

Designated by 12 is an imaging lens comprising movable lens groups 12a, 12b for zooming and a stationary lens group. The function of this imaging lens 12 is to reimage on a photo-film 13 an image of the fundus Ef formed through the objective lens 11. The central aperture 10a formed in the tilted mirror 10 serves as a diaphragm for photographing. But, a separate diaphragm may be provided in the vicinity of aperture 10a. The diaphragm, if any, is to be disposed conjugated with an image (not shown) of the slit plate 7 formed in the testing eye E with respect to the objective lens 11. These elements 11 to 13 including the diaphragm constitute a photographing system.

Designated by 14 is a jump-up mirror which is obliquely disposed when observing and which is retracted from the light path when photographing. 15 is a field lens disposed in the vicinity of the image plane F' which is conjugate with the image plane F with respect to the jump-up mirror 14. 16 is a light path deflecting mirror and 17 is an eyepiece. These elements 14 to 17 constitute a finder. If it is desired, a television camera may be provided in place of the eyepiece.

Mechanism for shifting the movable lens groups 12a and 12b is as follows:

A cam tube 20 has two cam slots 20a and 20b formed therein for variation and compensation respectively. The movable lens groups have pins directly connected therewith which engage with the cam slots 20a and 20b respectively. By rotating the cam tube 20, the position of each the lens group of 20a and 20b is determined depending upon the amount of cam. Although not shown in the drawing, the cam follower pins are also in engagement with a straight cam slot in parallel with the optical axis.

Secured on the circumferential surface of the cam tube 20 is a larger gear 21 in mesh with a smaller gear 22 for zooming drive. The smaller gear is driven by hand or by motor.

Designated by 23 is an end cam used for controlling the quantity of light emitted from the xenon tube 3. 24 is a cam follower comprising a roller 24a in contact with the cam 23, a lever 24b pivotally movable about a pivot 24c and a tension spring 24d. The roller 24a is attached to the one end of the lever 24b. The spring 24d biases the lever to rotate counter-clockwise so as to keep the roller in press contact with the cam surface. Generally designated by 25 is a variable resistor which is composed of a slide brush 25a fixed to another end of the lever 24a and a resistance plate 25b. The above mentioned end cam 23, follower 24 and variable resistor 25 constitute means for generating an electric signal representative of quantity or intensity of the emitted light to be changed in accordance with the change of magnification for photographing.

In the electric circuit connected to the incandescent lamp 1 there is a variable resistor 25' corresponding to the above described variable resistor 25. A power source is designated by 26. Since the resistance of variable resistor 25' varies according as zooming of the photographing system, the intensity of emitted light from the lamp 1 becomes weak when the picture angle is wide and it becomes strong when the angle is narrow. Therefore, the brightness of the image which the examiner views through the eyepiece is kept constant irrespective of zooming.

Now, the electric circuit connected to the xenon tube 3 will be described in detail.

Designated by 30 is a high voltage DC power source, 31 is a main condenser, 32 is a trigger circuit, 33 is a trigger switch, 34 is a light emission stopping circuit, 35 is a timing circuit and 36 is an operation switch for the timing circuit. The trigger switch 33 and operation switch 36 are turned on at the same time. The timing circuit includes a variable resistor 25" and other elements such as a condenser etc. not shown. When a certain time determined by the resistance of the resistor 25" has passed, the timing circuit generates a signal to operate the emission stopping circuit. The resistor 25" is of the same type as the above described 25. In practice, two resistors 25 are provided and one of them is used as 25' and the other as 25".

When the trigger switch 33 is turned on, the operating switch 36 is also turned on at the same time so that the trigger circuit 32 makes current flow from the main condenser to the xenon tube 3. As a result, the xenon tube is energized for emitting light. The emission of light continues for a time length determined by the resistance of resistor 25" and after the lapse of the time, the timing circuit 35 brings the stopping circuit 34 into operation so as to stop the power supply to the xenon tube 3 from the condenser 31. This makes the xenon tube stop emitting light. In this manner, the quantity of light emitted from the strobo tube is so controlled as to keep the exposure to photo-film constant irrespective of change of photographing magnification so long as the shutter speed remains unchanged.

The operation of the above described apparatus shown in FIG. 20 is as follows:

The examiner puts the lamp 1 on at first and then adjusts the cam tube 20 by driving the smaller gear 22 to rotate the larger gear 21 in mesh with the smaller one 20. The cam tube is adjusted, for example, to the position in which the lens groups 12a and 12b take a position for wide angle.

The beam of light emitted from the lamp 1 is once converged on the xenon tube by the condenser lens 2 and then it enters the condenser lens 4 diverging. The beam emerging from the lens 4 illuminates the slit plate 7 through the mirror 5. The beam of light passed through the ring slit aperture in the plate 7 is once converged on the tilted mirror 10 by the relay lens groups 8 and 9. The mirror 10 reflects it to the objective lens 11 which re-images the beam at a position close to the pupil of the testing eye E. After re-imaging, the beam of light illuminates the fundus Ef uniformly. The area of fundus illuminated by the light at this time corresponds to the wide angle photographing field of the photographing system.

The beam of light scatter-reflected upon the fundus Ef is once imaged by the objective lens 11 and thereafter it passes through the aperture 10a. The lens disposed behind the aperture 10a makes the beam converging. The convergent beam is reflected by the jump-up mirror 14 to the imaging plane F' on which the beam forms an image of the fundus. The image is observed by the examiner through the eyepiece 17.

When the examiner drives the smaller gear 22 to rotate the cam tube 20 up to the position in which the lens groups 12a and 12b take a narrow angle position, that is, a tele-side position for common zooming lens, the change of magnification is transformed into a cam amount of the cam surface 23 which is detected by the cam follower 24 so that the resistance value of the resistor 25' is changed accordingly. This change in resistance of the variable resistor 25' results in the corresponding increase in intensity of light of the lamp 1. Therefore, the brightness of visual field is maintained unchanged although the magnification for observation has been increased. There no longer occurs such a disadvantage that the visual field becomes dark when the optical system is shifted to the narrow angle position.

In the above described position of the apparatus, if the examiner operates a release switch (not shown) for taking a picture of the fundus, then the lamp 1 will be put off and the jump-up mirror 14 will be brought to its retracted position out of the light path. Switches 33 and 36 become turned on. A trigger signal is introduced into the xenon tube from the trigger circuit 32. Thus, the xenon tube 3 emits light. After a certain lighting time determined by the existing magnification for photographing has lapsed, the light emission stopping circuit 34 comes into operation to make the xenon tube stop emitting light. Thus, an optimum exposure is applied to the film 13. The path of light emitted from the xenon tube 3 is essentially the same as that of light emitted from the lamp 1.

Figure 21:
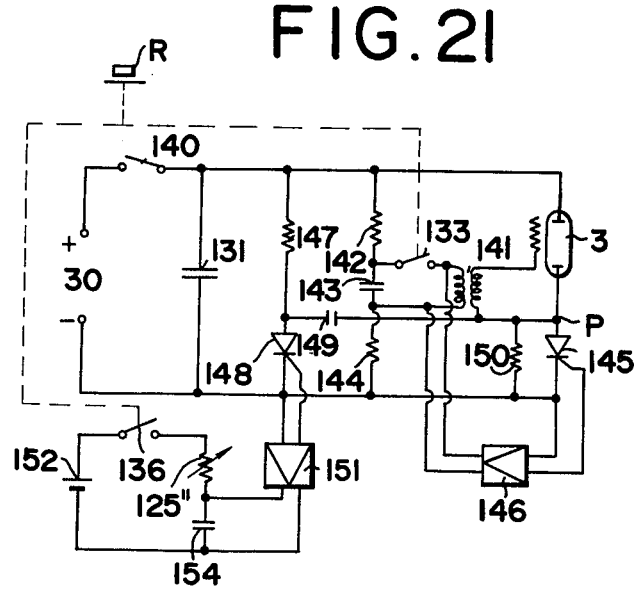
FIG. 21 is a block diagram of another electric circuit for controlling a light source for photographing.

FIG. 21 shows an example of control circuit for the strobo tube 3 making use of the principle of the known strobo control circuit.

In FIG. 21, arrangement of xenon tube 3, high voltage DC power source 30, main condenser 31, trigger switch 33, timing operation switch 36 and variable resistor 25 in linkage with the motion of zooming is the same as described above.

Designated by R is a release switch the function of which is to turn on switches 33 and 36 at the same time. 40 is a main switch, 41 is a trigger coil and 42 and 43 are high resistances. 43 is a condenser which applies its voltage at both terminals to the trigger coil 41. Designated by 45 is a first thyristor for switching to the gate of which a voltage of the condenser 43 is applied through an amplifying circuit 46.

47 is a resistor, 48 is a second thyristor, 49 is a condenser, 50 is a resistance. 51 is an amplifying circuit containing a Schmidt circuit, 52 is a DC power source and 54 is a condenser.

Operation of the above described circuit is as follows:
When the main switch is turned on, the power source 30 charges the condensers 31, 43 and 49. Releasing of the release switch R makes the trigger switch 33 turn on so that the voltage at both terminals of the condenser 43 is applied to the primary wiring of the trigger coil 41 and in the secondary wiring thereof there is produced a voltage. At the time when the produced voltage is applied to the xenon tube 3, the discharge voltage of the condenser 43 is applied to the amplifying circuit 46. The amplified voltage is applied to the gate of the first thyristor 45 so as to make it conductive. As a result, discharge of the main condenser 31 is effected between the anode and cathode of the first thyristor 45 so that the xenon tube is energized to emit light.

On the other hand, the releasing operation makes the timing operation switch 36 turn on so that current from the power source 52 flows into the condenser 54 through the variable resistor 25" which has a determined resistance value set therefor. After the lapse of time corresponding to the set value of resistance, the terminal voltage of the condenser 54 reaches a given level. At this time point, the Schmidt circuit in the amplifying circuit 51 comes into operation and applies an electric pulse to the gate of the second thyristor so as to make it conductive. This causes the condenser 49 to discharge through the second thyristor and resistance 50. Therefore, the voltage at the contact point P lowers and thereby the first thyristor 45 becomes non-conductive. As a result, the xenon lamp 3 stops emitting light.

As a modification of the embodiment shown in FIG. 20, a separate variable resistor may be provided in series with the variable resistor 25". By re-setting the resistance value of this additional variable resistor taking the sensitivity of film then used into consideration, it becomes possible to introduce the information of film sensitivity into the duration time of lighting of the xenon tube. Therefore, there is obtained the possibility of use of various films having different sensitivities relative to each other.

While the invention has been particularly shown and described with reference to preferred embodiments thereof, it will be understood by those skilled in the art that the foregoing and other changes in form and details can be made therein without departing from the spirit and scope of the invention.

I claim:
1. A variable magnification system with ability for compensation of change in quantity of light, said system comprising:
   a variable focal length optical system for imaging the radiation energy reflected from an object onto an image surface;
   detecting means, connected with said optical system, for detecting the focal length of said optical system;
   an observing finder system connected with said optical system;
   an illuminating system including at least one radiation source, for illuminating the object; and
   control means driven in response to said detecting means and adapted for controlling energy entering the image surface of said optical system.
2. A system as claimed in claim 1, wherein said control means is disposed within said illuminating means.
3. A system as claimed in claim 2, wherein said control means includes means the light transmissivity of which is variable.
4. A system as claimed in claim 3, wherein said means of variable light transmissivity is a filter the light transmissivity of which changes continuously and which is movable in the direction in which the light transmissivity changes.
5. A system as claimed in claim 3, wherein said means of variable light transmissivity is a filter the light transmissivity of which changes stepwise and which is movable in the direction in which the light transmissivity changes.
6. A system as claimed in claim 3, wherein said means of variable light transmissivity comprises two polarizing plates movable relative to each other.
7. A system as claimed in claim 3, wherein said means of variable light transmissivity includes light modulating means.
8. A system as claimed in claim 7, wherein said light modulating means is an electro optic cell.
9. A system as claimed in claim 2, wherein said control means is light screening means the light transmissive area of which is variable.
10. A system as claimed in claim 9, wherein said light screening means includes a screen plate provided with plural number of ring slits different in area from each other.
11. A system as claimed in claim 1, wherein said control means is an electric circuit for controlling energy flowing through said radiation source.

12. A system as claimed in claim 11, wherein said electric circuit changes the intensity of voltage applied to said radiation source.

13. A system as claimed in claim 12, wherein said electric circuit changes the time during which voltage is applied to said radiation source.

14. A system as claimed in claim 1, wherein said control means is disposed within said optical system.

15. A system as claimed in claim 14, said control means is light control means of variable aperture diameter.

16. A system as claimed in claim 15, wherein said light control means includes a screen plate having therein a plural number of apertures of different diameters.

17. A system as claimed in claim 1, wherein said optical system includes a fixed optical means opposed to an eye to be examined and a variable focus lens means; said observing system includes said optical system and an image transmitting system, at the image side of which optical system there is disposed a sensitive means; and said illuminating system includes a light source for observing, a light source for photographing, a light guiding system and said objective optical means.

18. A system as claimed in claim 17, wherein said variable focus lens means includes lens groups movable in the direction of optical axis.

19. A system as claimed in claim 17, wherein said variable focus lens means comprises imaging lens groups having different focal lengths and being removal.

20. A system as claimed in claim 17, wherein said variable focus lens means comprises a fixed lens group and exchangeable lens groups.

21. A system as claimed in claim 17, wherein said variable focus lens means comprises a fixed lens group and an attachment lens.

22. A system as claimed in claim 21, wherein said attachment lens is afocal.

23. A system as claimed in claim 17, wherein said light source for photographing is connected to a power supply controlling circuit which is driven by said detecting means.

24. A system as claimed in claim 23, wherein said power supply controlling circuit controls the duration time of power supply to said light source for photographing.

25. A system as claimed in claim 23, wherein said power supply controlling circuit controls the quantity of power supplied to said light source for photographing.

26. A variable magnification system comprising:
objective optical means adapted to be positioned for imaging an eye fundus to be inspected;
an image forming lens part, located at an image side of said objective optical means, for changing a focal length thereof;
photosensitive means located at an image side of said image forming lens part;
an illuminating system, having at least one radiation source, for illuminating through said objective optical means an eye fundus of the eye to be inspected;
driving means, connected with said lens part, for changing the focal length of said image forming lens part;
detecting means, connected with said driving means, for detecting the focal length of said image forming lens part; and
control means driven in response to said detecting means and adapted for controlling energy entering said photosensitive means.

27. A variable magnification system according to claim 26, wherein said image forming lens part includes two lens means movable in the direction of the optical axis thereof.

28. A variable magnification system according to claim 26, wherein said image forming lens part includes an attachment lens attachable across the optical axis thereof.

29. A system as claimed in claim 26, wherein said control means is disposed within said illuminating means.

30. A system as claimed in claim 29, wherein said control means includes means the light transmissivity of which is variable.

31. A system as claimed in claim 29, wherein said control means is light screening means the light transmissive area of which is variable.

32. A system as claimed in claim 26, wherein said control means is an electric circuit for controlling energy flowing through said radiation source.

33. A system as claimed in claim 32, wherein said electric circuit changes the intensity of voltage applied to said radiation source.

34. A system as claimed in claim 33, wherein said electric circuit changes the time during which voltage is applied to said radiation source.

* * * * *

UNITED STATES PATENT AND TRADEMARK OFFICE
CERTIFICATE OF CORRECTION

PATENT NO. : 4,265,518
DATED : May 5, 1981
INVENTOR(S) : ISAO MATSUMURA

It is certified that error appears in the above—identified patent and that said Letters Patent is hereby corrected as shown below:

Column 1, line 23, after "a" delete "such; line 52, after "a" (first occurrence), insert --light--.

Column 3, line 7, after "12b", insert --are--;

Column 4, line 10, after "intensities", insert --relative to--;

Column 6, line 37, "terminal" should be --terminals--

Column 7, line 37, "23" should be --123--; line 38, "24" should be --124--; line 39, "24a" should be --124a--; line 40, "23" should be --123--; same line, "24b" should be --124b--; line 41, "24c" should be --124c--; same line, "24a" should be --124a--; line 42, "24d" should be --124d--; line 45, "25" should be --125--; line 46, "25a" should be --125a--; line 47, "24a" should be --124a--;
same line, "25b" should be --125b--; line 48, "23" should be --123--; same line, "24" should be --124--; line 49, "25" should be --125--; line 54, "25'" should be --125'--; line 55, "25" should be --125--; line 56, "26" should be --126--;

UNITED STATES PATENT AND TRADEMARK OFFICE
CERTIFICATE OF CORRECTION

PATENT NO. : 4,265,518

DATED : May 5, 1981

INVENTOR(S) : ISAO MATSUMURA

It is certified that error appears in the above—identified patent and that said Letters Patent is hereby corrected as shown below:

Column 7, line 57, "25'" should be --125'--; line 66, "30" should be --130--; line 67, "32" should be --132--; same line, "33" should be --133--; line 67, "31" should be --131--; line 68, "34" should be --134--; same line "35" should be --135--.

Column 8, line 2, "33" should be --133--; line 3, "36" should be --136--; line 4, "25"" should be --125"--; line 7, "25"" should be --125"--; line 8, "25""should be --125"--; line 9, "25" should be --125--; line 10, "25 " should be --125 --; line 11, "25'" should be --125'--; line 11, "25"" should be --125"--; line 12, "33" should read --133--; line 13, "36" should be --136--; line 14, "32" should be --132--; line 18, "25"" should be --125"--; line 19, "35" should be --135--; same line "34" should be --134--; line 21, "31" should be --131--.

UNITED STATES PATENT AND TRADEMARK OFFICE
CERTIFICATE OF CORRECTION

PATENT NO. : 4,265,518

DATED : May 5, 1981

INVENTOR(S) : ISAO MATSUMURA

It is certified that error appears in the above—identified patent and that said Letters Patent is hereby corrected as shown below:

Column 9, line 8, "33" should be --133--; line 9, "36" should be --136--; line 10, "32" should be --132--; line 14, "34" should be --134--; line 23, "31" should be --131--; line 24, "33" should be --133--; same line "36" should be --136--; line 25, "25" should be --125--; line 28, "33" should be --133--; same line "36" should be --136--; line 29, "41" should be --141--; same line "40" should be --140--; same line, "43" should be --143--; line 30, "43" should be --143--; line 31, "41" should be --141--; line 32, "45" should be --145--; line 33, "43" should be --143--; line 34, "46" should be --146--; line 35, "47" should be --147--; same line "48" should be --148--; same line, "49" should be --149--; line 36, "50" should be --150--; same line, "51" should be --151--; line 37, "52" should be --152--; line 38, "54" should be --154--; line 41, "31" should be --131--; same line, "43" should be --143--; same line, "49" should be --149--; line 42, "33" should be --133--; line 43, "43" should be --143--; line 44, "41" should be --141--; line 48, "43" should be --143--;

UNITED STATES PATENT AND TRADEMARK OFFICE
CERTIFICATE OF CORRECTION

PATENT NO. : 4,265,518

DATED : May 5, 1981

INVENTOR(S) : ISAO MATSUMURA

It is certified that error appears in the above—identified patent and that said Letters Patent is hereby corrected as shown below:

Column 9, line 48, "46" should be --146--; line 50, "45" should be --145--; line 51, "31" should be --131--; line 52, "45" should be --145--; line 55, "36" should be --136--; line 56, "52" should be --152--; same line, "54" should be --154--; line 60, "54" should be --154--; line 62, "51" should be --151--; line 64, "49" should be --149--; line 66, "50" should be --150--; line 67, "45" should be --145--.

Column 10, line 3, "25"" should be --125"--.

Signed and Sealed this

First Day of December 1981

[SEAL]

Attest:

GERALD J. MOSSINGHOFF

Attesting Officer

Commissioner of Patents and Trademarks